United States Patent [19]

Cornell et al.

[11] 4,246,123
[45] Jan. 20, 1981

[54] FLUID COLLECTION DEVICE WITH PHASE PARTITIONING MEANS

[75] Inventors: William D. Cornell, Ballwin; Victor H. Wetzel, Bridgeton, both of Mo.

[73] Assignee: Sherwood Medical Industries Inc., St. Louis, Mo.

[21] Appl. No.: 31,818

[22] Filed: Apr. 20, 1979

[51] Int. Cl.³ .............................................. D01D 21/26
[52] U.S. Cl. .................................. 210/782; 210/789; 210/515; 210/DIG. 24; 210/927
[58] Field of Search ................... 210/83, 84, 514–516, 210/DIG. 23, DIG. 24; 233/1 A

[56] References Cited

U.S. PATENT DOCUMENTS

| 3,852,194 | 12/1974 | Zine, Jr. | 210/83 |
| 3,920,549 | 11/1975 | Gigliello, Jr. | 210/83 |
| 3,957,654 | 5/1976 | Akres | 210/516 |
| 3,976,579 | 8/1976 | Bennett | 210/516 |
| 3,981,804 | 9/1976 | Gigliello | 210/516 |
| 3,997,442 | 12/1976 | Gigliello et al. | 210/83 |
| 4,021,340 | 5/1977 | Zine, Jr. | 210/83 |
| 4,046,699 | 9/1977 | Zine, Jr. | 210/DIG. 23 |
| 4,055,501 | 10/1977 | Cornell | 210/DIG. 23 |
| 4,088,582 | 5/1978 | Muaty et al. | 210/516 |

Primary Examiner—John Adee
Attorney, Agent, or Firm—Stanley N. Garber; William R. O'Meara

[57] ABSTRACT

A fluid collection device is provided which includes a container for receiving a liquid, such as blood, that is centrifugally separable into relatively light and heavy phases, and a phase partitioning device in the container. The partitioning device includes a thixotropic gel-like material adjacent one end of the container having a specific gravity between the specific gravities of the light and heavy phases, and a piston member having an outlet in communication with the sealant so that during centrifugation of the device, centrifugal forces cause the piston to pressurize the sealant and force the sealant through the outlet toward the interface of the phases with sealant forming a partition between the separated phases.

29 Claims, 5 Drawing Figures

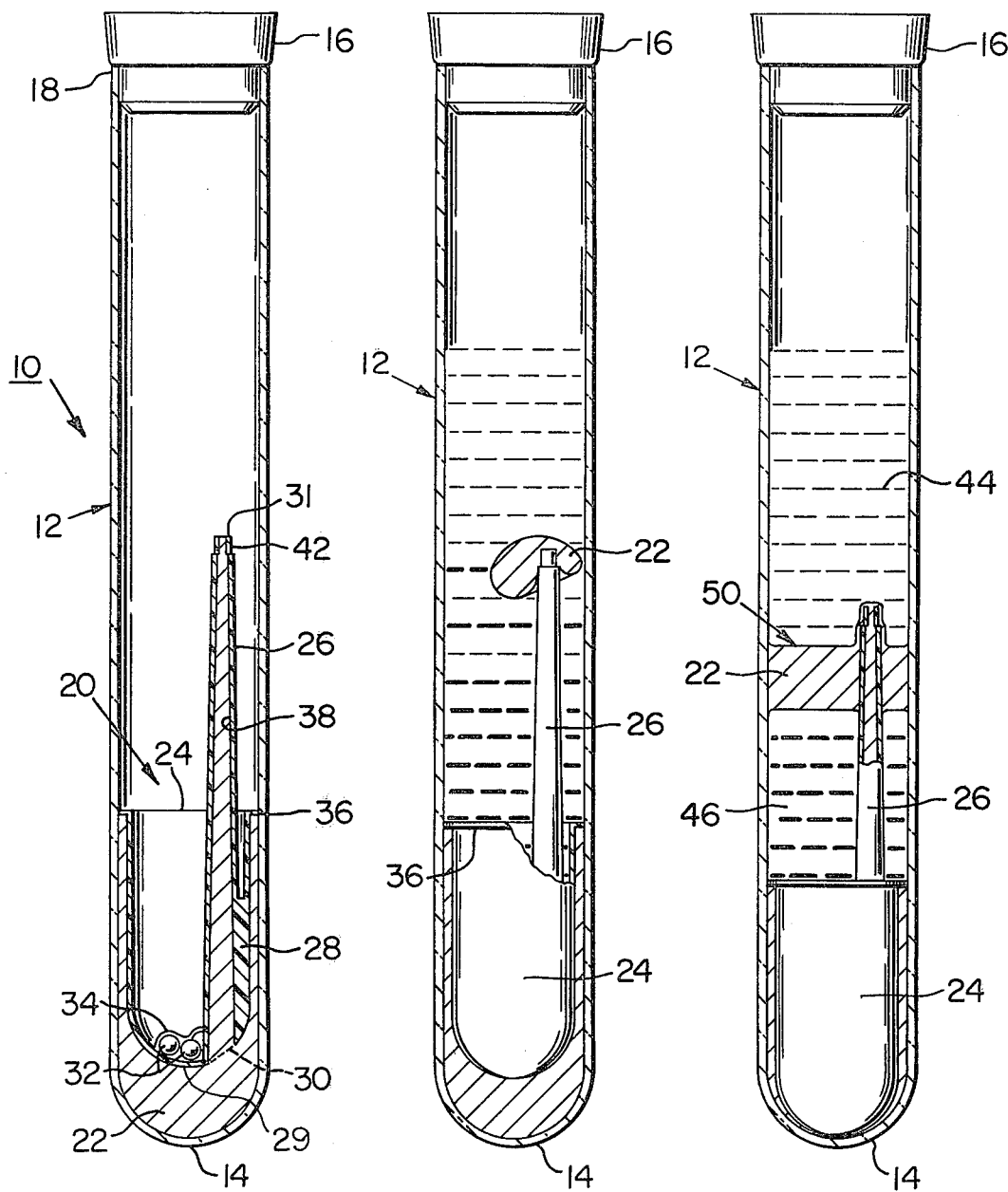
FIG. 1
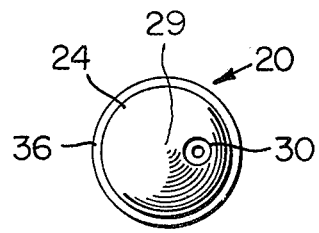
FIG. 2
FIG. 4
FIG. 5
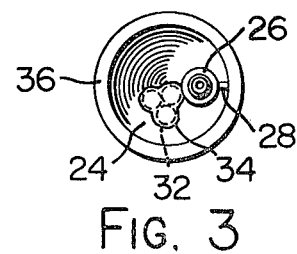
FIG. 3

FLUID COLLECTION DEVICE WITH PHASE PARTITIONING MEANS

BACKGROUND OF THE INVENTION

This invention relates to fluid collection devices, and more particularly, to blood collection devices having means for partitioning the relatively light phase from the relatively heavy phase.

When taking blood samples for test purposes, whole blood is generally drawn into an evacuated collection tube and the tube subsequently centrifuged to separate the blood into its relatively light phase, serum or plasma, and its heavier cellular phase. Blood phase separators or portitioning devices have been used to provide a barrier between the separated phases until the light phase is removed for clinical testing.

Many types of blood phase partitioning devices have been proposed, all with varying degrees of success. A relatively simple partitioning arrangement includes the use of a quantity of gel-like thixotropic material having a specific gravity intermediate the specific gravities of the light and heavy blood phases so that during centrifugation and phase separation, the material automatically flows to the interface of the two phases and forms a partition or barrier between the phases. Various gel-like thixotropic materials or sealants are now well known. For example, in U.S. Pat. No. 3,852,194, a mixture of silicone and hydrophobic silicon dioxide powders is used to form a partition between the separated phases. In U.S. Pat. Nos. 4,021,340; 4,088,582 and 4,055,501 mixtures including liquid polybutene polymer and silicon dioxide powders are used as phase partitioning materials.

A problem in the use of phase partitioning sealants has been that desired flow characteristics have not always been obtained. For example, in some cases the sealant may form a partition too soon and trap blood cells in the light phase, causing contamination. For certain tests, such contamination can result in unreliable or inaccurate test results. On the other hand, in some cases the sealant may remain in its initial location, adhering to the collection tube, and not flow during centrifugation to the interface of the two phases, thus failing to form a partition. Where the relatively small difference in specific gravities of the sealant and heavy phase is relied upon to provide the force necessary to cause the sealant to flow toward the interface, reliable flow characteristics may not always be obtained.

In some arrangements the sealant flows upwardly in the collection tube, interfering with the downward flow of cells or blood clots during centrifugation. This may result in the sealant carrying cells to the interface or trapping them so that they remain in contact with the separated light phase. Also, the impact of cells with the sealant during centrifugation is believed to cause cell homolysis and an artificial increase in lactic dehydrogenase (LDH). Where this occurs, the LDH result is, of course, inaccurate.

SUMMARY OF THE INVENTION

Accordingly, it is an object of the present invention to provide a fluid collection device for receiving a liquid, such as blood, that is separable into relatively light and heavy phases and which reduces or avoids the above disadvantages.

Another object is to provide a blood collection device utilizing a thixotropic sealant to form a phase partition during phase separation and centrifugation and wherein desirable flow characteristics are readily obtained while cell contamination of the separated light phase and artificially caused LDH are minimized.

In accordance with one form of the invention, a fluid collection device for receiving a liquid centrifugally separable into relatively light and heavy phases is provided with a quantity of a sealant material having a specific gravity between the specific gravities of the separated relatively light and heavy phases. A piston having a specific gravity greater than the heavy phase is disposed in the device adjacent the sealant, and an upwardly extending passage connects with the sealant. The piston is movable to force sealant upwardly through the passage during phase separation and centrifugation of the device so that the sealant forms a partition between the separated phases after centrifugation.

These, as well as other objects and advantages of the present invention, will become apparent from the following detailed description and drawing.

BRIEF DESCRIPTION OF THE DRAWING

FIG. 1 is an elevational cross-sectional view of a blood collection device in accordance with a preferred embodiment of the present invention;

FIG. 2 is a bottom plan view of the phase partitioning device of FIG. 1;

FIG. 3 is a top plan view of the phase partitioning device of FIG. 1;

FIG. 4 is an elevational cross-sectional view of the collection device of FIG. 1 after blood has been drawn into the device and while it is being centrifuged to separate the relatively light and heavy phases of blood; and FIG. 5 is an elevational view of the collection device of FIG. 1 after complete blood separation and centrifugation.

DESCRIPTION OF THE PREFERRED EMBODIMENT

Referring now to the drawing, and particularly to FIGS. 1-3, a blood collection device 10 is shown including a blood collection container or tube 12 having a lower end 14 shown as an integrally formed portion of the tube, a stopper 16 closing the upper end 18 of the tube, and a blood phase partitioning device 20 disposed within tube 12. Stopper 16 is made of a suitable rubber which is pierceable by a needle cannula for introducing a sample of blood into the tube and is self-sealing when the needle cannula is removed. Tube 12 is preferably made of glass and is evacuated to provide a negative pressure within the tube for facilitating the flow of blood into the tube.

The partitioning device 20 includes a sealant material 22 which is a thixotropic gel-like material having a specific gravity intermediate the specific gravity of separated relatively light phase, serum or plasma, and the specific gravity of the relatively heavy cellular phase of blood so that the sealant will seek the interface of the separated phases during phase separation. The sealant 22 may have a specific gravity between about 1.03 and 1.06. The material 22, which will be explained in greater detail hereafter, is shown disposed adjacent the bottom end 14 of tube 12.

Device 20 also includes a piston member 24 and a tube or standpipe 26. The piston and standpipe may be injection molded as a single part using a suitable plastic such as polyethylene, styrene acrylonitrile, or other relatively rigid plastic material. While piston 24 and pipe 26 may be separately formed and then connected together by a suitable cement, if desired, the walls of pipe 26 are shown connected at the bottom integrally with the piston 24 and are also connected by a web 28 near the bottom for structural strength. The pipe 26 extends through the bottom wall 29 of piston 24 and has a bottom opening or sealant inlet 30 and an upper opening or sealant outlet 31. The specific gravity of the piston 24 may be readily varied by adding weights 32, for example, in the form of metal balls which are connected to the bottom of piston 24 such as by an adhesive or cement 34 such as of the epoxy type. Instead of or in addition to weights 32, the material or plastic from which the piston is made may have a material mixed with it, such as barium sulfate, to increase the specific gravity of the piston to a desired value. The piston is shown as a cylindrical, cup-shaped member with the bottom wall 29 rounded or downwardly convex and generally complementary in shape to the inner bottom wall of tube 12.

At the upper peripheral edge of the piston 24, is a radial flange or lip 36 which frictionally engages the inner walls of the tube and provides a seal against the flow of sealant 22 past the lip. In assembling the collection device 10, the sealant 22 may be deposited in the bottom of the tube 12 and then the piston and standpipe unit moved downwardly in the tube and into the sealant 22 until sealant fills the space between the piston and the tube wall up to the lip 36 and further until the pipe 26 is completely filled with the sealant. It will be apparent that as the piston is pushed toward tube end 14 and into the sealant, the sealant will move into the lower opening 30 in the pipe 26 and be forced upwardly in the sealant flow passage indicated at 38 of the pipe. After the phase partitioning device 20 is located in place, as in FIG. 1, the stopper 16 may be inserted into the upper open end 18 of the tube 12 while in an air-evacuated chamber so as to provide a suitable negative pressure within tube 12 to facilitate the drawing of a blood sample.

A sample of blood may be drawn into the collection tube 12 by using a double-ended needle cannula, such as provided by a conventional needle holder and tube guide. For example, after the distal end of the cannula is inserted into the vein of a patient, the device 10 is moved onto the proximal end of the cannula until the cannula pierces stopper 16, whereupon whole blood flows into tube 12. The filled tube is subsequently placed in a centrifuge such that the lower end 14 will be radially outwardly of the stopper and axis of rotation of the centrifuge during centrifugation. As is well known, if it is desired to separate serum, a blood clot is formed before the collection device is centrifuged.

The specific gravity of the partitioning device 20 is made greater than the specific gravity of the sealant 22 and the specific gravity of the heavier cellular phase. By providing the device 20 with a sufficiently high specific gravity, the driving force for displacing the sealant 22 can be made high enough to provide flow of sealant upwardly in the pipe 26 under typical centrifugal forces. Thus, a suitably high driving force or pressurization of the sealant may be readily obtained by simply providing the device 20 with a desired specific gravity, such as by weighting it or forming it of relatively heavy material. In order to control or regulate the flow rate of sealant into the passage 38 and out the upper open end 31 of pipe 26, the upper end of the pipe may be provided with a restriction such as indicated at 42, that is, with a portion of substantially smaller cross-section or diameter than the average diameter of the passage 38. In this manner, relatively large sealant driving forces are available, while the control and rate of flow of the sealant can be readily effected by the forming of passage 38 with a desired inside diameter and/or restriction 42. This arrangement provides desirable sealant flow characteristics during phase separation and centrifugation so as to obtain a light phase, serum or plasma, sample of high quality, making it possible to obtain accurate test results.

In FIG. 4, the tube 12 is illustrated as being filled with a whole blood sample while the phase separation is taking place in a centrifuge. As the piston descends in the sealant, the sealant flows out the upper open end 31 of the pipe 26 as indicated. The height of the pipe 26 is such that it is above that point in the tube 12 at which the upper level of the cellular phase is expected to be formed. Since the upper level of the cellular phase will vary from sample to sample, that is, because the hematocrit between samples differs, the standpipe is preferably made long enough to be substantially above the upper level of the cellular phase after centrifugation, even when there is a high hematocrit. Preferably, the pipe will extend above the main barrier or into the light phase.

As the centrifugation continues, the partitioning device 20 moves downwardly into the sealant 22, causing the continuous flow of sealant from the bottom of the tube up through the passage 38 and out the upper end 31 of the pipe 26. Since the sealant has a specific gravity intermediate the specific gravities of the separated lighter and heavier phases, which phases are indicated at 44 and 46 in FIG. 5, the sealant will seek the interface between the separated phases and finally form a partition 50 between the two phases as indicated in FIG. 5. In FIG. 5, the piston 24 is shown engaged with the bottom of the tube 12 and with the completed partition 50 providing a semi-solid or substantially non-flowable liquid impervious seal or barrier between the two phases.

The pipe 26 is located off-center or radially displaced from the longitudinal axis of tube 12 so that it is closely adjacent the sidewall of the tube 12, as well as the sidewall of the piston member 24. In this way, in the case of serum separation, blood clot movement toward the bottom end 14 is not interfered with by the standpipe 26, that is, the blood clot itself can readily move downwardly past the upper end of the pipe 26 and move into the piston 24, allowing complete phase separation to take place without delay. Also, since the clot readily moves by the off-centered pipe, there is less engagement between cells and the standpipe, and reduced hemolysis of blood cells due to such engagement, thereby tending to reduce the amount of LDH produced by the phase separation process.

Since relatively high sealant pressurization is readily obtained with the phase partitioning device 20, the standpipe 26 may be made relatively long, that is, with the upper end well within the upper portion of the tube 12 so that the sealant 22 will flow out of the passage 38, into the light phase, and then downwardly (rather than flowing upwardly through the cellular phase) toward its final position. The last portion of the sealant to issue from passage 38 when phase separation is essentially completed will flow downwardly from the light phase and provide a layer or zone of the sealant barrier that is substantially free of any blood cells and will cover any cells that might be late to settle, to thereby ensure that cells are not in contact with the light phase after phase separation.

On specific example of a useful sealant is described in U.S. Pat. No. 4,088,582 and includes 100 parts by weight of liquid polybutene (Polybutene Grade 24—Chevron Chemical Company of San Francisco, Calif.), 20 parts by weight of hydrophillic silica powder (Min-U-Sil 10, PGS, subsidiary of ITT, Pittsburg, Penn.), and 9 parts by weight of a hydrophobic silica powder (Aerosil R-972, Degussa Inc., Pigments Division, New York, N.Y.). The latter silica powder was produced by a process including flame hydrolysis of silicate, and then made hydrophobic by reacting the silica with dimethyl dichlorosilane and steam. By varying the proportions of polybutene and silica powders, desired static and dynamic viscosities and specific gravity characteristics can be obtained.

One example of a desirable construction may include the following items:
16×127 mm standard glass tube (I.D. 13.6 mm)
85% draw (percentage of tube fill)
1 cm sealant barrier height (vol. 1.5 ml)
Piston and standpipe height 8.8 cm Since some sealant remains in the standpipe and around the piston, and the barrier is about 1.5 ml, a total of about 2 ml of sealant may be used.

The above example device is effective for hematocrits up to about 75%.

While the standpipe 26 provides the passage 38 through the piston 24 and produces the advantages pointed out herein, a piston similar to piston 24 but without a standpipe may be used. In such case, a passage or opening, such as a hole through the bottom wall of the piston, may be provided so that sealant will be squeezed upwardly through the hole during centrifugation and phase separation. The sealant will pass through the piston toward its final position between the separated phases. A desired flow rate for a given sealant material can be obtained by choosing a suitably sized opening or passage through the piston and choosing a suitable specific gravity for the piston.

As various changes could be made in the above construction without departing from the scope of the invention, it is intended that all matter contained in the description or shown in the accompanying drawing shall be interpreted as illustrative and not in a limiting sense.

What is claimed is:

1. A fluid collection device for receiving a liquid separable into relatively light and heavy phases during centrifugation of the device comprising an elongate container for receiving the liquid and having an upper end closed by a stopper and a lower closed end, and phase partitioning means including a sealant material in an initial location in said container adjacent said lower end, said sealant material having a specific gravity intermediate the specific gravities of said light and heavy phases and flowable upwardly in response to centrifugation of the device from said initial location to a position between the separated phases to provide a partition therebetween, and relatively rigid elongate passage means having inner sidewalls, an inlet adjacent the lower end thereof communicating with said sealant material when said sealant material is in said initial location, and an outlet spaced upwardly from said inlet for passing said sealant material upwardly within said passage means from said initial location toward said position between the separated phases, said passage means being offset from the longitudinal axis of said container to reduce the interference between the downwardly flowing heavy phase and said passage means, said passage means sidewalls preventing contact of said sealant material with said container and the heavy phase during movement of said sealant material upwardly in said passage means, said passage means inlet being disposed adjacent said lower end of said container before and after phase separation.

2. The device of claim 1 wherein said partitioning means further includes piston means having a specific gravity greater than that of the heavy phase and disposed initially above said sealant material, said piston means being movable toward said lower end in response to centrifugal forces during centrifugal phase separation and is constructed to pressurize said sealant material and cause it to flow upwardly in said passage means toward said position.

3. A fluid collection device for receiving a liquid separable into relatively high and heavy phases during centrifugation of the device comprising an elongate container for receiving the liquid and having upper and lower closed ends, and phase partitioning means including a thixotropic sealant material in an initial location in said container adjacent said lower end, said sealant material having a specific gravity intermediate the specific gravities of said light and heavy phases and flowable during centrifugation of the device from said location to a position between the separated phases to provide a partition therebetween, passage means having sidewalls, an inlet in communication with said sealant material when said sealant is in said location, an outlet upwardly spaced from said lower end and said inlet for passing said sealant from said location to said position between the separated phases, and piston means having a specific gravity greater than that of the heavy phase and initially disposed above said sealant material, said piston means being movable downwardly toward said lower end in response to centrifugal forces during centrifugal phase separation to pressurize said sealant material and cause it to flow upwardly in said passage means with said passage means sidewalls preventing contact of said sealant with said cellular phase and said container during movement of said sealant material in said passage means, said piston and said passage means inlet being disposed adjacent said lower end of said container before and after phase separation.

4. The device of claim 1, 2 or 3 wherein said passage means comprises a standpipe.

5. The device of claim 4 wherein said inlet and outlet are openings in said standpipe and said standpipe extends from said sealant material upwardly to a point in said container such that said outlet is above the upper level of the separated heavy phase.

6. The device of claim 5 wherein said standpipe is sized such that said outlet is at a point in said container, after centrifugation and phase separation, which is above the upper level of said partition.

7. The device of claim 2 or 3 wherein said passage means extends through said piston means.

8. The device of claim 4 wherein said standpipe is connected to said piston means.

9. The device of claim 8 wherein said inlet and outlet are in opposite end portions of said standpipe, said inlet being in the bottom wall of said piston means.

10. The device of claim 8 wherein said piston means comprises a cylindrical member having an annular flange sealingly engaging the side walls of said container substantially preventing the flow of said sealant material upwardly between said container and said piston means.

11. The device of claim 10 wherein said standpipe is integrally connected to said piston means, and said standpipe and piston means are of plastic.

12. The device of claim 10 wherein said piston and standpipe means are integral, and said piston is generally cup-shaped with said flange at the upper end thereof, said piston having a downwardly convex bottom wall, and said inlet is in said bottom wall.

13. A blood collection device for receiving whole blood separable into a relatively lower density phase and a higher density cellular phase during centrifugation of the device comprising an elongate container for receiving the blood and having upper and lower closed ends, and phase partitioning means including a sealant material in an initial location in said container adjacent said lower end, said sealant material having a specific gravity intermediate the specific gravities of said lower and higher density phases and flowable during centrifugation of the device from said location to a position between the separated phases to provide a partition therebetween, and piston means having a specific gravity greater than that of the higher density phase and means defining an opening therethrough, said piston means being disposed above said sealant material in said container in sealing engagement with the inner sidewalls of said container and movable toward said lower end of said container in response to centrifugal forces during centrifugal phase separation to pressurize said sealant material and cause it to flow upwardly through said opening toward said position between the separated phases.

14. The device of claim 13 wherein said piston is a cylindrical member having a peripheral flange frictionally sealingly engaging the inner sidewalls of said container, said piston being slidable downwardly toward said lower closed end of said container during centrifugation and remaining adjacent said lower end after phase separation.

15. The device of claim 14 wherein said piston is generally cup-shaped and has a downwardly convex bottom wall.

16. The device of claim 13 wherein said container device is adapted to contain a lower density blood phase which is serum and a cellular phase having a blood clot, and said opening defining means includes a standpipe connected to said piston means and having a sealant flow passage in fluid communication with said sealant material and having an outlet above the upper level of the separated higher density phase, said standpipe having its longitudinal axis offset from the longitudinal axis of said container to avoid interfering with the movement of the blood clot toward said lower end of said container.

17. The device of claims 1, 2, or 3, wherein said passage means has a fluid-flow restriction therein for restricting rate of flow of said sealant from its initial location toward its final position between the separated phases.

18. The device of claims 1, 2, or 3 wherein said liquid is blood, and said sealant material has a specific gravity between the specific gravities of the relatively higher density cellular phase of blood and the lighter density phase of blood.

19. The device of claim 1, 3 or 13 wherein the specific gravity of said sealant material is between about 1.03 and 1.06.

20. The device of claim 12 wherein said upper and of said container is closed by a stopper which is needle-pierceable for introducing whole blood into said container.

21. The device of claim 20 wherein said container has a negative pressure therein.

22. The device of claim 1 or 13 wherein said sealant material is a gel-like thixotropic material.

23. A method of separating whole blood into its lower density and higher density phases and providing a partition between the separated phases comprising the steps of providing in the lower end portion of a container a thixotropic gel-like sealant having a specific gravity between those of the lower and higher density phases, a piston above the sealant having a specific gravity greater than that of the higher density phase, and an elongate standpipe having an inlet adjacent the lower end of the container connected in communication with the sealant and having an outlet in the upper portion thereof, introducing whole blood into the container, centrifuging the blood-filled container so that the higher density phase separates to the lower portion of the container and the piston moves downwardly to force sealant upwardly within the standpipe and from the outlet into the container exteriorly of the standpipe, and continuing centrifugation of the blood-filled container at least until the piston moves downwardly to the lower end of the container and the phases are completely separated and the sealant provides a partition between the separated phases and with the standpipe inlet adjacent the lower end of the container.

24. The method of claim 23 wherein said sealant is inserted into the container and then said piston is inserted into the container above the sealant in sealing sliding engagement with the inner sidewalls of the container.

25. The method of claim 23 or 24 wherein said piston and standpipe are integrally formed.

26. The method of claim 23 wherein said container is evacuated to facilitate said step of introducing whole blood into the container.

27. the method of claim 24 or 26 wherein said standpipe is disposed closely adjacent the side wall of the container with its longer axis radially offset from the longer axis of the container.

28. The device of claim 1 wherein said elongate passage means comprises a pipe with the lower end thereof adjacent said sealant material and said lower end of said container and the upper end of said pipe located at a point in said container above the upper level of the heavy phase when separated.

29. The device of claim 2 or 3 wherein said piston is sealingly engageable said slidable along the inner sidewall of said container to pressurize said sealant material and said sealant material is in contact with the inner side of said container.

* * * * *